US006998604B2

(12) United States Patent
Nishizawa et al.

(10) Patent No.: US 6,998,604 B2
(45) Date of Patent: Feb. 14, 2006

(54) APPARATUS FOR MEASURING ABSORPTION DOSE DISTRIBUTION

(75) Inventors: Hiroshi Nishizawa, Tokyo (JP); Tomoyuki Shiomi, Tokyo (JP); Satoshi Senoo, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 197 days.

(21) Appl. No.: 10/359,697

(22) Filed: Feb. 7, 2003

(65) Prior Publication Data

US 2003/0150983 A1    Aug. 14, 2003

(30) Foreign Application Priority Data

Feb. 14, 2002    (JP)    .............................. 2002-036461

(51) Int. Cl.
    *G01T 1/20*    (2006.01)
(52) U.S. Cl. .................................. 250/252.1; 250/367
(58) Field of Classification Search ............ 250/252.1, 250/367, 368, 369, 363.09, 370.08; 378/65, 378/207, 19, 98.8
    See application file for complete search history.

(56) References Cited

U.S. PATENT DOCUMENTS

| | | | | |
|---|---|---|---|---|
| 4,109,150 A | * | 8/1978 | Martone et al. ............ | 250/368 |
| 4,243,886 A | * | 1/1981 | Untermyer, II ......... | 250/390.01 |
| 4,379,967 A | * | 4/1983 | McIntyre ................. | 250/227.2 |
| 4,510,394 A | * | 4/1985 | Allemand et al. ....... | 250/483.1 |
| 4,675,526 A | * | 6/1987 | Rogers et al. ......... | 250/363.02 |
| 5,856,673 A | | 1/1999 | Ikegami et al. | |
| 6,066,851 A | * | 5/2000 | Madono et al. ............. | 250/367 |
| 6,225,622 B1 | * | 5/2001 | Navarro ................... | 250/252.1 |
| 6,396,898 B1 | * | 5/2002 | Saito et al. .................... | 378/4 |
| 6,594,336 B1 | * | 7/2003 | Nishizawa et al. ........... | 378/65 |
| 6,652,809 B1 | * | 11/2003 | Comley et al. .......... | 422/82.05 |
| 2002/0131552 A1 | | 9/2002 | Nishizawa et al. | |

OTHER PUBLICATIONS

Brannen et al. "Electron Dosimetry in Phantoms using Thin Scintillator", Physics depart., University of Western Ontario, London, Ontario, Canada, issue 1 (Jul. 1960).*
Beddar et al. "Water-equivalent plastic scintillation detectors for high-energy beam dosimetry: I. Physical characteristic and theoretical consoderations", Depart. of Medical Physics, Univerisyt of Wisconsin Medical School, madison, WI (Feb. 27, 1992).*
"IMRT/3D QA Phantom" *MED-TEC.*

* cited by examiner

*Primary Examiner*—Otilia Gabor
(74) *Attorney, Agent, or Firm*—Leydig, Voit & Mayer, Ltd.

(57) ABSTRACT

An apparatus for measuring absorption dose distribution may be used for radiotherapy, such as intensity modulated radiotherapy and radiosurgery. In the apparatus, measurement or evaluation of the distribution of the radiated dose within a phantom can be achieved accurately and in a relatively short length of time. The apparatus includes a phantom with a plastic plate scintillator having a thickness within the range of 0.15 to 1 mm and plastic blocks sandwiching the plastic scintillator, and an image analyzer. At least one of the plastic blocks is transparent and the image analyzer measures a pattern of intensity distribution of light emitted from the plastic scintillator when the phantom is irradiated.

14 Claims, 8 Drawing Sheets

APPARATUS FOR MEASURING ABSORPTION DOSE DISTRIBUTION

BACKGROUND OF THE INVENTION

1. Field of the Invention

The present invention relates to an apparatus for accurately and quickly measuring absorbed dose distribution in a phantom that is used in the course of a radiotherapeutic treatment of cancer using X-rays, particle beams such as electron beams or the like.

2. Description of the Prior Art

In intensity modulated radiotherapy (IMRT), a radiotherapeutic treatment, it has been a general practice to irradiate a patient by changing the field profile of radiation and, also, the direction of incidence of radiation so that the cumulative absorption dose of the radiation may be proportionated to an affected zone of the patient. Accordingly, IMRT has been recognized having merit in that irradiation can be concentrated on an affected zone to enhance radiotherapy.

However, when it comes to performance of the IMT, a treatment plan has to be set up in which irradiating conditions required for the affected zone to be irradiated in a predetermined absorption dose distribution are to be formulated. The validity of the treatment plan, however, requires experiment-based verification or evaluation and, for this purpose, the absorption dose measuring apparatus for IMRT (hereinafter referred to as "IMRT-dedicated absorption dosimeter") is generally utilized.

Figure 14:
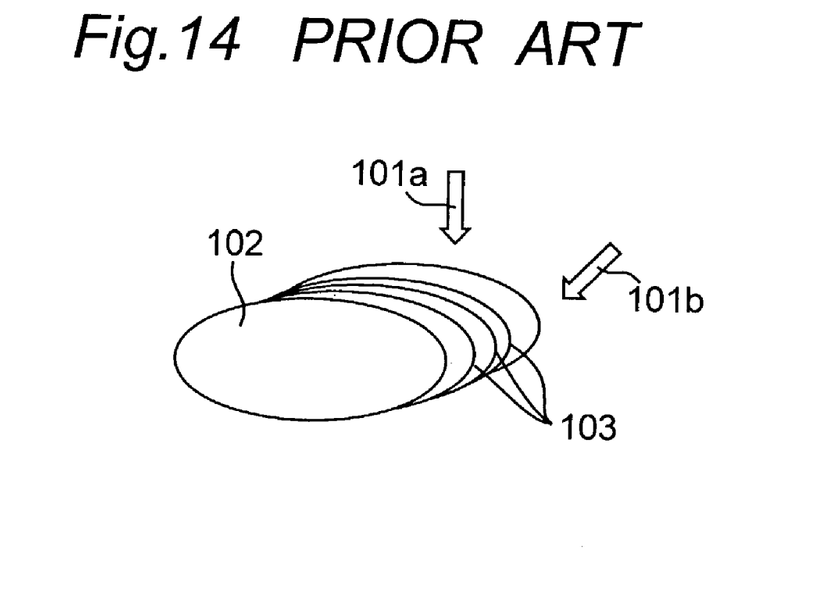
FIG. 14 is a diagram showing the manner of measurement of the absorption dose distribution with a conventional IMRT-dedicated absorption dosimeter.

Measurement of the absorption dose distribution performed by the conventional IMRT-dedicated absorption dosimeter will be described hereinafter with reference to FIG. 14. As shown in FIG. 14, the conventional IMRT-dedicated absorption dosimeter includes a plurality of phantoms 102 and a corresponding number of X-ray films 103 respectively sandwiched between neighboring phantoms 102. With this conventional IMRT-dedicated absorption dosimeter, the phantoms 102 are irradiated with radiation 101a and 101b such as particle beams, X-rays, electron beams, or the like and, as a result thereof, the X-ray films 103 sandwiched between neighboring phantoms 102 are exposed due to the interaction with the radiation 101a and 101b. By measuring a distribution of the optical density in the X-ray films 103, a two-dimensional absorption dose distribution at various positions on the X-ray films 103 can be obtained. Then, a three-dimensional absorption dose distribution within the phantoms 102 is obtained based on the two-dimensional absorption dose distribution so measured with respect to all of the X-ray films 103.

Figure 15:
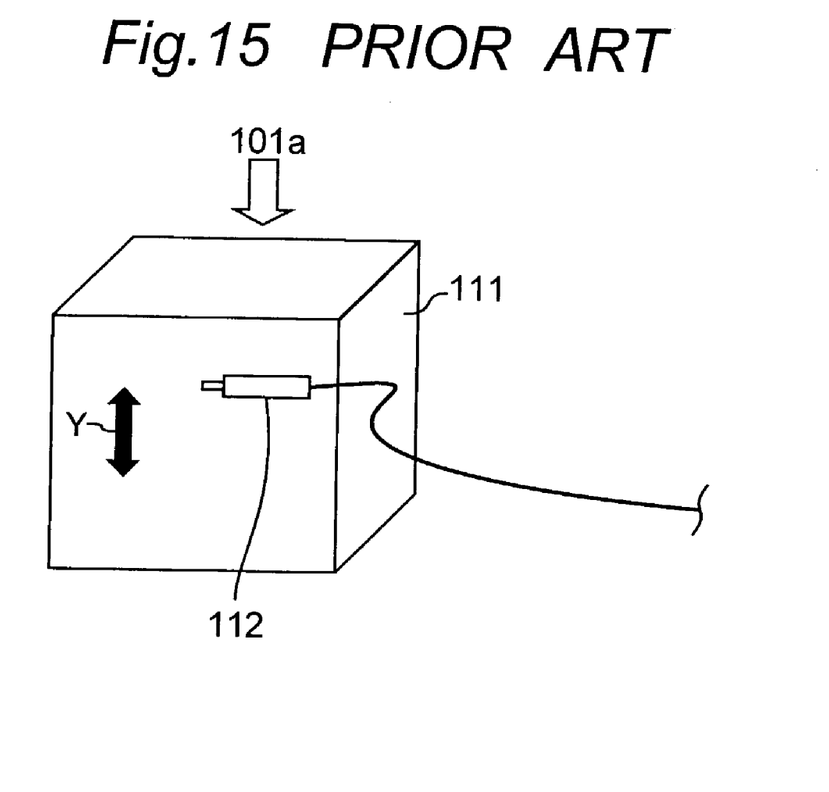
FIG. 15 is a diagram showing the manner of measurement of the absorption dose distribution in conventional Radiosurgery.

Radiosurgery is also known in the art as an alternative choice of the radiotherapeutics. This Radiosurgery makes use of a slender beam of a diameter with a few cm$^2$ of the area of the radiating field. Hereinafter, measurement of the absorption dose distribution with the radiation dosimeter for the Radiosurgery will be described with reference to FIG. 15. As shown in FIG. 15, measurement with the radiation dosimeter for the Radiosurgery requires the use of a water phantom 111 in which a microchamber 112 is inserted so that the microchamber 112 can be scanned within the water phantom 111 in a direction shown by the arrow Y to measure a distribution of absorbed dose.

However, the IMRT-dedicated absorption dosimeter utilizing the X-ray films as shown in FIG. 14 has a problem in that since the absorption characteristic of the X-ray films differs considerably from that of a human body, accurate measurement of the absorption dose pattern is difficult to achieve. Also, depending on the manufacturing lots and/or developing conditions of the X-ray films, the output tends to vary even though those X-ray films have absorbed an equal amount of radiation, resulting in difficulty in achieving measurement accuracy. Also, the work of developing the exposed X-ray films and measuring the optical density requires a substantial amount of labor and a substantial amount of time.

In the practice of the IMRT, an irregular radiation field is defined with the use of a multi-leaf collimator. In such case, the edge of the resultant radiation field has a generally wedge-shaped configuration not larger than a few millimeters and requires the use of a measuring instrument having a spatial resolving power not larger than a few millimeters if an accurate distribution of radiated dose is to be measured. Similarly, even measurement of the absorbed dose distribution for Radiosurgery requires the use of a measuring instrument having a spatial resolving power not larger than a few millimeters so that a beam used to irradiate an extremely small radiation field is to be measured. However, scanning within the water phantom of the microchamber having a spatial resolving power not larger than a few millimeters requires a substantial amount of labor and a substantial amount of time. Yet, there is an additional problem in that since the sensitive region is so small, the output current is so low as to result in a low signal-to-noise (S/N) ratio.

SUMMARY OF THE INVENTION

The present invention has been devised to substantially eliminate the above discussed problems and has an object to provide an apparatus for measuring absorption dose distribution (hereinafter simply referred to as "distribution-measuring apparatus"), for use in radiotherapy such as IMRT and Radiosurgery wherein measurement or evaluation, of the distribution of the radiated dose within the phantom can be achieved accurately and in a relatively short time.

In order to accomplish the above described object of the present invention, the present invention provides a distribution-measuring apparatus which includes a phantom and an image analyzer. The phantom is constructed of a plate-type plastic scintillator, and first and second plastic blocks. The plastic scintillator has a thickness within the range of 0.15 to 1 mm. The first and second plastic blocks are positioned on respective sides of the plastic scintillator in the thickness direction thereof so as to sandwich the plastic scintillator therebetween. At least one of the first and second plastic blocks is transparent. The image analyzer measures a pattern of intensity distribution of light emitted from the plastic scintillator when the phantom is irradiated with radiation. It is to be noted that each of the first and second plastic blocks referred to above may be constructed of a plurality of sub-blocks.

In the distribution-measuring apparatus according to the present invention, since the plate-type plastic scintillator emits light proportional to the absorbed dose and the resultant intensity distribution of the light is measured by the image analyzer, it is possible to highly accurately and quickly measure the two-dimensional absorption dose distribution at the position of the plastic scintillator. Also, when the thickness of the plastic scintillator is chosen to be within the range of 0.15 to 1 mm, a particular value of which may be set in consideration of a surface condition of the plastic scintillator, it is possible to reduce light diffusion and light scattering and, therefore, the spatial resolving power of the distribution-measuring apparatus can be set to substantially 1 mm. For this reason, the therapeutic accuracy in radiotherapy can be increased.

BRIEF DESCRIPTION OF THE DRAWINGS

The present invention will become readily understood from the following description of preferred embodiments thereof made with reference to the accompanying drawings, in which like parts are designated by like reference numeral and in which.

DESCRIPTION OF THE EMBODIMENTS (First Embodiment)

Figure 1:
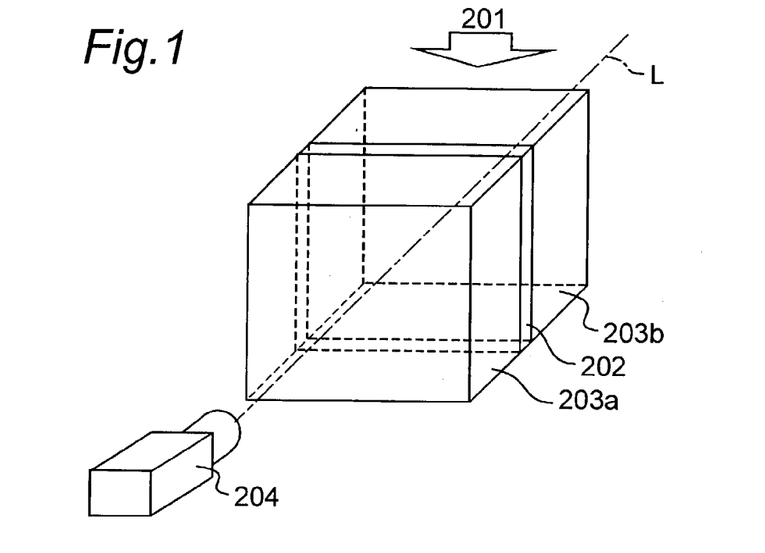
FIG. 1 is a perspective view of a distribution-measuring apparatus according to a first preferred embodiment of the present invention.

FIG. 1 illustrates the overall structure of a distribution-measuring apparatus (an apparatus for measuring absorption dose distribution) according to the first embodiment of the present invention. As shown therein, the distribution-measuring apparatus includes a phantom constructed of a plate-shaped plastic scintillator 202, a transparent plastic block 203a and a plastic block 203b and adapted to be irradiated with radiation 201 such as X-rays or particle beams such as electron beams. It is to be noted that the plastic blocks 203a and 203b are, when viewed in a direction shown by a straight line L, that is, in a direction of thickness of the plastic scintillator 202 (hereinafter referred to as "scintillator thickness direction"), arranged with opposite end faces (confronting in the scintillator thickness direction) of the plastic scintillator 202 sandwiched between the plastic blocks 203a and 203b.

When the phantom is irradiated with the radiation 201 from a direction substantially perpendicular to the scintillator thickness direction, the intensity distribution of light (the emitted light intensity distribution) that is emitted from one of the opposite end faces of the plastic scintillator 202 is measured with an image analyzer 204 such as, for example, a CCD camera.

Each of the plastic scintillator 202 and plastic blocks 203a and 203b forming respective parts of the phantom has a radiation absorption characteristic that can be regarded equivalent to that of the tissue of a human body. The plastic scintillator 202 emits from various regions thereof, light of an intensity proportional to the absorption dose at a position corresponding to each region. Accordingly, the light emitted from the plastic scintillator 202 in its entirety gives rise to a two-dimensional light intensity distribution on the end face of the plastic scintillator 202. This light intensity distribution corresponds to the two-dimensional absorption dose distribution within the plastic scintillator 202. Accordingly, by measuring this two-dimensional light intensity distribution with the image analyzer 204, the two-dimensional absorption dose distribution at such position where the plastic scintillator 202 is located can be immediately measured.

If the distribution-measuring apparatus is provided with a conversion coefficient (or a conversion table) used to convert the amount of light emitted from the plastic scintillator 202 into an absolute value of the absorption dose rate, it is possible to simultaneously measure not only the two-dimensional absorption dose distribution, but. also the absolute value of the absorption dose rate. Also, if measurement is carried over the entire period of radiation and the amount of emitted light is integrated with respect to time, it is also possible to obtain the absolute value of the integrated absorption dose.

In the distribution-measuring apparatus according to the present invention, the plastic scintillator 202 has an extremely small thickness as compared with that of the conventionally used scintillator and is chosen to be within the range of 0.15 to 1 mm. Hereinafter, the reason for selection of the particular scintillator thickness will be described in more detail. In the first place, however, influences the thickness of the plastic scintillator 202 brings about on the intensity distribution of light emitted from the plastic scintillator 202 will be discussed.

Figure 2A:
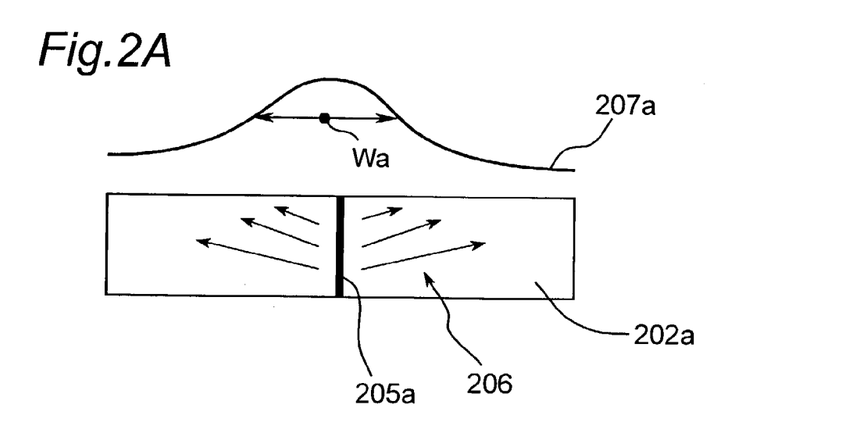
FIGS. 2A and 2B show intensity distribution characteristic of light on a scintillator surface when the thickness of a plastic scintillator (i.e., a scintillator made of a plastic material) is large and small, respectively.
Figure 2B:
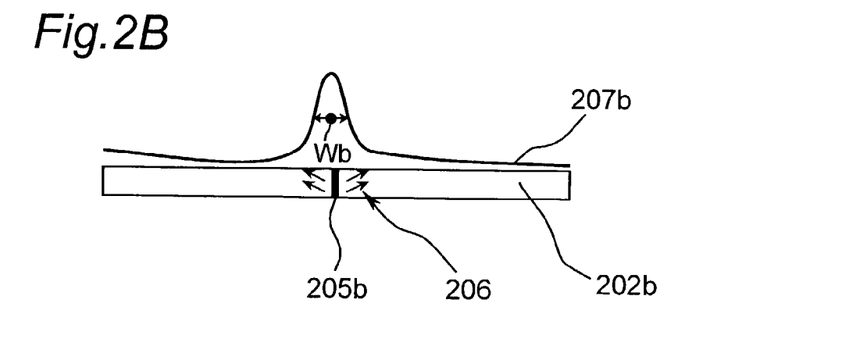

FIG. 2A illustrates the thick plate-type plastic scintillator 202a together with the intensity distribution of light emitted from one end face (hereinafter referred to as "scintillator surface") of such scintillator 202a. FIG. 2B illustrates the thin plate-type plastic scintillator 202b together with the intensity distribution of light emitted from one end face or scintillator surface of such scintillator 202b. It is to be noted that the term "thick" is intended to mean a thickness greater than about 1 mm whereas the term "thin" is intended to mean a thickness not greater than about 1 mm.

As shown in FIGS. 2A and 2B, it is assumed that light is emitted from a straight site 205a and 205b extending in the scintillator thickness direction within the respective plastic scintillator 202a and 202b. The light formed by this light emission radiates isotropically from the point of emission thereof. It is, however, to be noted that in FIGS. 2A and 2B, only paths of travel 206 of light towards one end face side of each of the plastic scintillator 202a and 202b are shown for the sake of brevity.

As is clear from FIG. 2A, since the thick plastic scintillator 202a exhibits a large diffusion of light, the full width at one-half the maximum intensity, Wa, of the light intensity distribution 207a at the scintillator surface becomes large. It is to be noted that the term "full width of half maximum" is intended to mean the width of a region at which the light intensity assumes a value equal to or greater than one-half the maximum light intensity. On the other hand, as is clear from FIG. 2B, with the thin plastic scintillator 202b, since it exhibits a small diffusion of light, the full width of half maximum Wb of the light intensity distribution 207b at the scintillator surface is small.

Accordingly, in order to increase (or enhance) the spatial resolving power of the distribution-measuring apparatus in a direction of spreading of the scintillator surface, it is necessary to reduce the thickness of the plastic scintillator 202. On the other hand, as will be described later, it is generally requisite for the distribution-measuring apparatus to have a spatial resolving power of about 1 mm. As such, in order for the distribution-measuring apparatus to have a spatial resolving power of about 1 mm, it has been found as a result of a series of calculations and experiments conducted by the inventors of the present invention that depending on the condition of the scintillator surface, it is necessary for the plastic scintillator 202 to have a thickness within the range of 0.15 and 1 mm.

The smaller the thickness is of the plastic scintillator 202, the more can the spatial resolving power of the distribution-measuring apparatus be increased. However, care must be taken that if the thickness of the plastic scintillator 202 is excessively reduced, the following inconveniences may result in. Specifically, it is difficult to manufacture a thin scintillator plate of a uniform thickness. If the thickness of the plastic scintillator 202 is not uniform, the position dependency of the thickness, that is, the amount of light emitted will be so considerable as to result in reduction in functionality as a analyzing instrument. On the other hand, if the thickness is not uniform, a gap will be formed between the plastic scintillator 202 and each of the plastic blocks 203a and 203b positioned on respective sides thereof Because of those reasons, it will become spatially heterogeneous and deformation will occur in the dose distribution. Also, where the plastic scintillator 202 is thin, the amount of light emitted will decrease, accompanied by reduction in signal-to-noise ratio.

The specific reason for selection of the plastic scintillator 202 to a value within the range of 0.15 to 1 mm will now be discussed on the basis of the result of calculations and experiments conducted by the inventors of the present invention. As hereinabove described, it is generally required for the distribution-measuring apparatus to have a spatial resolving power of about 1 mm, and this is attributable to the fact that the spatial resolving power required in radiotherapy is about 1 mm.

The following enumerates factors that affects the treatment accuracy or the spatial accuracy in the current radiotherapeutic cancer treatment (See, for example, literature "Standard Method of Radiation Dose Measurement for Localized Radiation").

(1) Limit of the diagnostic spatial resolving power is about 1.7 mm.
(2) Limit of positioning accuracy of therapeutic equipments is about 1.0 mm.
(3) Displacement in position resulting from involuntary motion of internal organs of a patient is about 1.0 mm.
(4) No boundary between the cancer-affected tissue and the normal tissue is clear.

Even if the problems associated with (1) and (4) were to be resolved as a result of improvement of the diagnostic technique and the problem associated with (2) were to be resolved as a result of improvement in precision of the therapeutic equipments, the problem associated with (3) will remain unsolved and will remain an inevitable factor. Accordingly, it may be said that the accuracy required in radiotherapy is limited to 1 mm.

On the other hand, the distribution-measuring apparatus is designed to improve the therapeutic accuracy in radiotherapy. By way of example, in Radiosurgery which is one of the radiotherapeutic cancer treatment methods, since the area of the radiation field is small, spatial inclination of the absorption dose distribution is large. Since if a detector has a large noticeable dimension, the output will be an average of the noticeable region, it is not possible to achieve an accurate measurement of the absorption dose distribution. Accordingly, the smaller the noticeable dimension of the detector is, the better. However, in view of the fact that as hereinbefore discussed the limit of the therapeutic accuracy in radiotherapy is limited to about 1 mm, it may be concluded that about 1 mm is sufficient for the spatial resolving power of the distribution-measuring apparatus.

In radiotherapeutic treatment of a cancer it is desirable to focus the radiation on only cancer-affected cells, not normal cells, in order to minimize any side effects. In such case, if an error in radiation dosage exceeds 5%, therapeutic results will be adversely affected. If an error in spatial resolving power exceeds the limit of 1 mm, the error in radiation dosage will often exceed 5%. Accordingly, in the distribution-measuring apparatus it is necessary for the dose distribution to be measured with the spatial resolving power of not greater than 1 mm.

Even in the IMRT, since an irregular radiation field is defined with the use of a multi-leaf collimator and a similar problem arises in the radiation field edge, the spatial resolving power is required to be not greater than 1 mm.

As a result of optical simulation or simulation of the position resolving power, the inventors of the present invention have found that in order for the spatial resolving power of the distribution-measuring apparatus to be about 1 mm, the thickness of the plastic scintillator 202 has to be set to a value within the range of 0.15 to 1.0 mm depending on the surface condition of the scintillator plate. Hereinafter, procedures for and result of calculation used during the optical simulation or simulation of the position resolving power will be described.

As described hereinabove, it is necessary for the spatial resolving power of the distribution-measuring apparatus for Radiosurgery to be not greater than 1 mm. As an apparatus for measuring the absorption dose distribution within phantom, such a depth dose distribution measuring apparatus as disclosed in the Japanese Patent No. 3102342 is known, in which scintillation fibers are bundled in a block form. However, it has been that since the fibers employed in this known depth dose distribution measuring apparatus have a length of about 10 mm, it is not possible to reduce the spatial resolving power down to a value not greater than 1 mm unless any resort is taken. It is to be noted that although it is contemplated to cut the fibers employed in the conventional depth dose distribution measuring apparatus down to a length of 1 mm, this will bring about a problem associated with considerable increase of the cost of manufacture.

In view of the foregoing, desk calculation has been done to determine if the spatial resolving power at the dose distribution measuring site can be reduced to a value not greater than 1 mm when an easy-to-manufacture, inexpensive plate-type plastic scintillator is employed. This calculation is done by the following procedures.

Specifically, as shown in FIG. 2A, when an arbitrary straight light emitting site 205a is available within the plate-type plastic scintillator 202a, a pattern of distribution of light reaching the scintillator surface (the end face of the plastic scintillator 202a is calculated according to Monte Carlo simulation. In this present invention, a pattern of distribution of light reaching the scintillator surface when light from the straight light emitting side 205a within the plastic scintillator 202a is isotropically radiated was calculated with the thickness of the plastic scintillator 202a (hereinafter referred to as "scintillator thickness") being varied.

Results of calculation are as follows.

Figure 3:
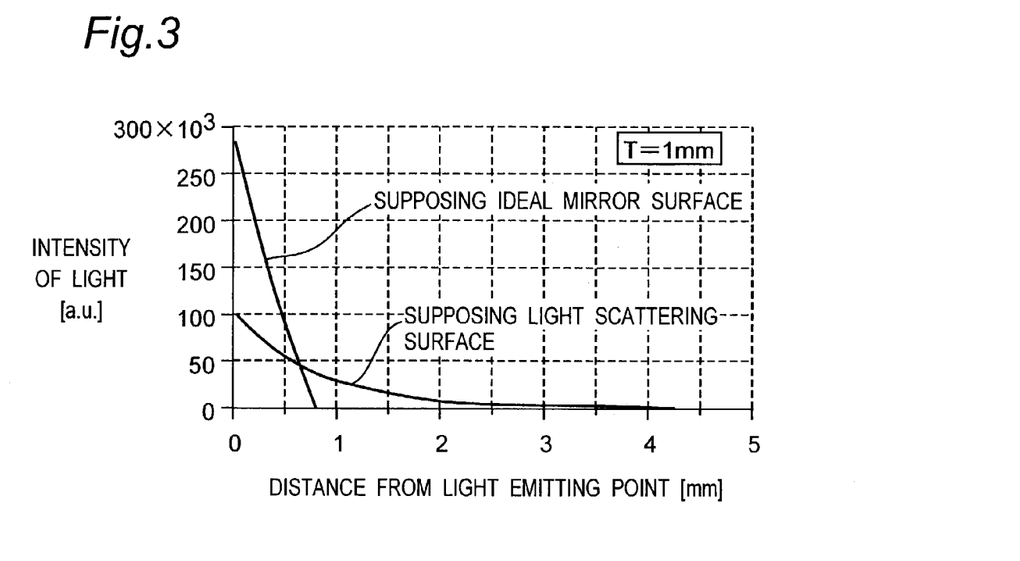
FIG. 3 is a graph showing the intensity distribution of light on the scintillator surface when the thickness of the scintillator is 1 mm.

Results of the calculation of the distribution of light on the scintillator surface obtained when the scintillator thickness T is 1 mm are shown in FIG. 3. When a condition of the scintillator surface is different (for example, whether it be an ideal optical mirror surface or a light scattering surface), the angle of emergence of the light to the outside of the plastic scintillator is correspondingly different and, accordingly a different pattern of light amount results in. Also, when the scintillator thickness T is to be determined, a crosstalk (that is, the extent to which when light emits from a certain point, the light emitting from this certain point affects other points) occurring in a direction perpendicular to the scintillator thickness direction must be taken into consideration.

Figure 4:
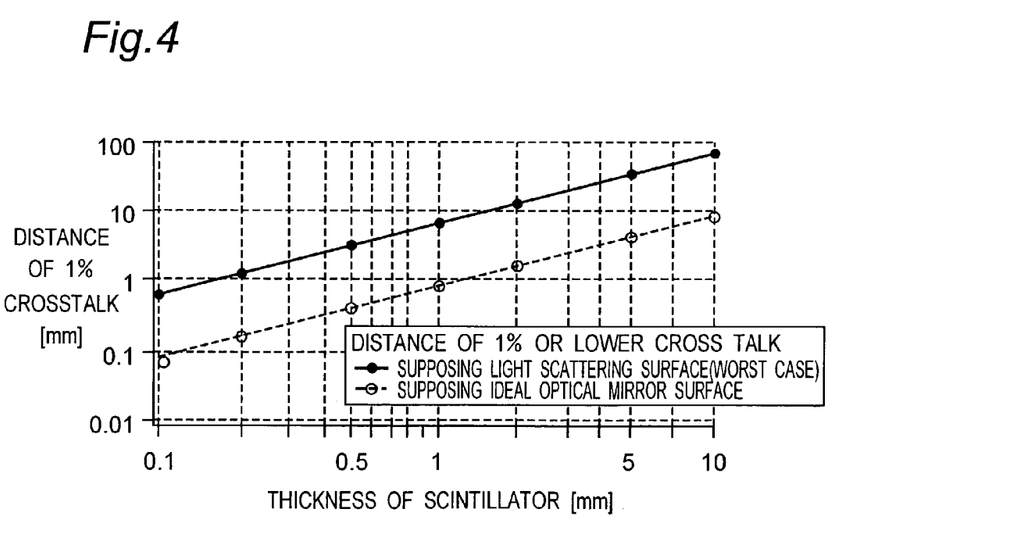
FIG. 4 is a graph showing the distance from a light emitting point to the point at which the crosstalk attains 1%.

Therefore, assuming that the required specification of the distribution-measuring apparatus is such that the spatial resolving power is 1 mm and the crosstalk is not higher than 1%, the distance at which the 1% or lower crosstalk occurs must be not greater than 1 mm. FIG. 4 illustrates the distance from the light emitting point (the light emitting position) to the point at which the 1% or lower crosstalk occurs. As shown in FIG. 4, this distance is not greater than 1.2 mm in the case of an ideal optical mirror surface (in an optimum case) or not greater than 0.15 mm in the case of a light scattering surface (in an undesirable case).

It is to be noted that the foregoing calculation results are those obtained for the spatial resolving power in the direction perpendicular to the scintillator thickness. Also, as described hereinbefore, the spatial resolving power of the absorption dose distribution measuring apparatus in the scintillator thickness direction must be not greater than 1 mm. Accordingly, the scintillator thickness T must be not greater than 1.0 mm in the case of the ideal optical mirror surface and not greater than 0.15 mm in the case of the light scattering surface.

Therefore, according to the results of the simulated calculation discussed above, it will readily be seen that if in the distribution-measuring apparatus utilizing the plate-type plastic scintillator 202, the scintillator thickness is chosen to be within the range of 0.15 to 1.0 mm depending on the surface condition of the plastic scintillator 202, the spatial resolving power thereof will be 1 mm. Hence, in the distribution-measuring apparatus according to this first embodiment of the present invention, the thickness of the plastic scintillator 202 is set to a value within the range of 0.15 to 1.0 mm depending on the surface condition thereof (Second Embodiment)

The second embodiment of the present invention will be described with reference to FIGS. 5A and 5B. The distribution-measuring apparatus according to this embodiment has numerous features common with the distribution-measuring apparatus according to the first embodiment of the present invention. Accordingly, in the following description, features and/or components similar to those of the distribution-measuring apparatus according to the first embodiment are not described to avoid repetition thereof and, instead, only differences from that according to the first embodiment will be described. Specifically, in the distribution-measuring apparatus according to the second embodiment, the surfaces of the plastic scintillator are polished to represent surfaces similar to an optical mirror surface, and other features and/or components thereof are substantially identical with those in the distribution-measuring apparatus according to the first embodiment.

Figure 5A:
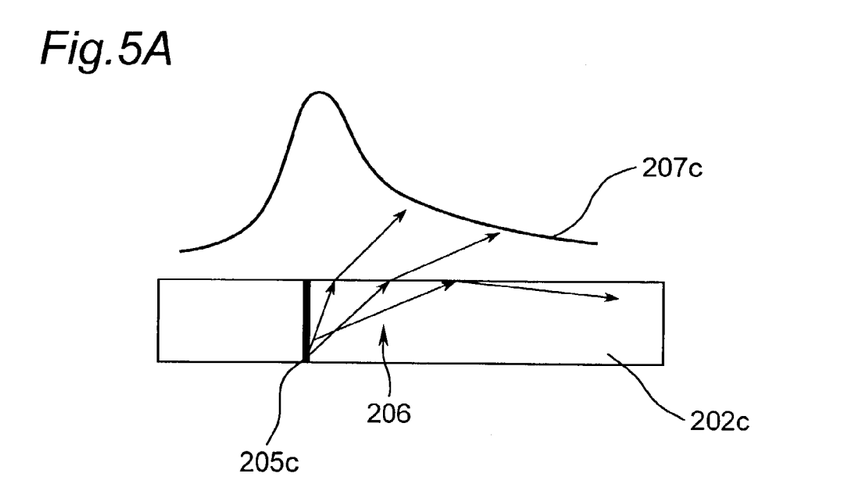
FIGS. 5A and 5B are diagrams showing the intensity distribution characteristics of light on the scintillator surface when the surface of the plastic scintillator is polished to a substantial mirror surface and frosted, respectively.

FIG. 5A illustrates a plate-type plastic scintillator 202c having at least one surface polished to represent a surface similar to the optical mirror surface together with a pattern of intensity distribution of light 207c emitted from the scintillator surface. On the other hand, FIG. 5B illustrates a plate-type plastic scintillator 202d having at least one surface ground to represent a frosted surface together with a pattern of intensity distribution of light 207d emitted from the scintillator surface.

Figure 5B:
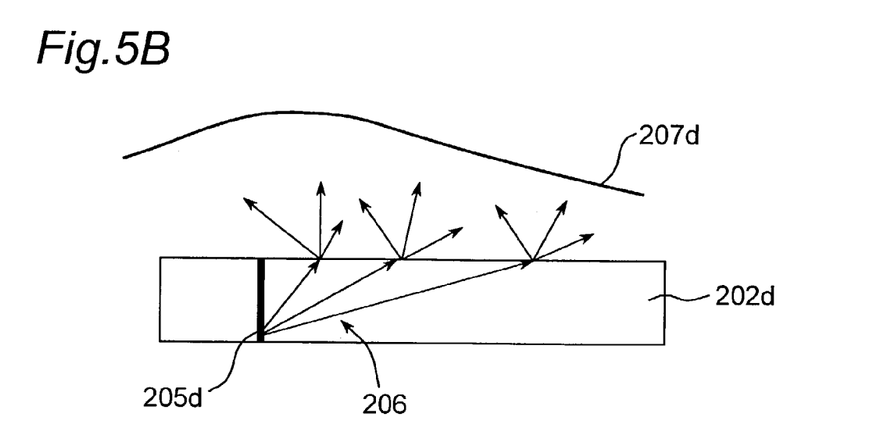

As shown in FIGS. 5A and 5B, it is assumed that light is emitted from a straight site 205c and 205d extending in the scintillator thickness direction within the respective plastic scintillator 202c and 202d. The light formed by this light emission radiates isotropically from the point of emission thereof and it is, however, to be noted that in these figures, only paths of travel 206 of light towards one end face side of each of the plastic scintillator 202c and 202d are shown for the sake of brevity.

As is clear from FIG. 5A, in the plastic scintillator 202c polished to represent a surface similar to an optical mirror surface, when light reaches the scintillator surface, some of the light emerges outwardly from the plastic scintillator 202c and some are reflected internally within the plastic scintillator, according to the principle of reflection and refraction. While light measured by the image analyzer 204 is that emerging outwardly from the plastic scintillator 202c, the amount of light emerging outwardly from the plastic scintillator 202c decreases with increase of the distance from the light emitting point particularly where the scintillator surface is polished to represent a surface similar to the optical mirror surface. Because of this, the intensity distribution of light 207c at the scintillator surface exhibits an extremely small full width of half maximum. Thus, polishing the scintillator surface so as to represent a surface similar to the optical mirror surface is effective to increase the spatial resolving power.

In contrast thereto, as clearly shown in FIG. 5B, with the plastic scintillator 202d having the scintillator surface ground to represent a frosted surface, light reaching the scintillator surface undergoes scattering on the scintillator surface and, therefore, the amount of light emerging outwardly from the plastic scintillator 202d will not decrease with increase of the distance from the light emitting point. Because of this, the intensity distribution of light 207d at the scintillator surface results in increase of the full width of half maximum with the spatial resolving power consequently reduced.

(Third Embodiment)

The third embodiment of the present invention will be described with reference to FIG. 6. It is however to be noted that the distribution-measuring apparatus according to this embodiment has numerous features common with the distribution-measuring apparatus according to the first embodiment of the present invention and, accordingly, in the following description, features and/or components similar to those of the distribution-measuring apparatus according to the first embodiment are not described to avoid repetition thereof and, instead, only differences from that according to the first embodiment will be described. Specifically, in the distribution-measuring apparatus according to the third embodiment, the wavelength of light emitted from the plastic scintillator is set to a visible region ranging from a green region to a red region, while other features and/or components thereof are substantially identical with those in the distribution-measuring apparatus according to the first embodiment.

While the plate-type plastic scintillator 202 emits light (hereinafter referred to as "scintillation light") in a quantity proportional to the absorbed dose, at the same time the plastic scintillator 202 and the transparent plastic block 203a emit Cerenkov light. Although the amount of the Cerenkov light emitted is smaller than that of the scintillation light, it will constitute a noise in measurement of the absorbed dose since the amount of the Cerenkov light emitted is not proportional to the absorbed dose.

Figure 6:
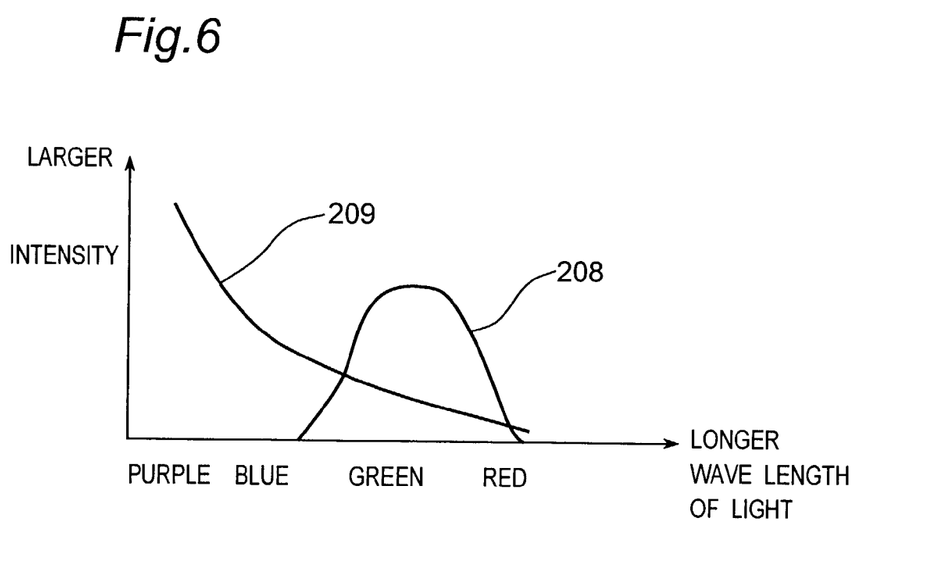
FIG. 6 is a graph showing the spectrum of light emitted from a plate-type plastic scintillator and the spectrum of Cerenkov light, in a distribution-measuring apparatus according to a third preferred embodiment of the present invention.

Accordingly, as shown in FIG. 6, in order to suppress the noise attributable to the Cerenkov light down to a value as low as possible, the plastic scintillator 202 is chosen to have a spectrum (an emitted light wavelength) 208 lying within a spectral region of wavelength as long as possible, that is, within the visible region of light ranging from a green spectral region to a red spectral region. As can be seen from FIG. 6, the spectrum 209 of the Cerenkov light tends to exhibit a high strength at a wavelength as short as possible and, accordingly, arrangement has been made to reduce the noise resulting from the Cerenkov light by increasing the wavelength of the scintillation light so that the strength of the Cerenkov light may be relatively low as compared with that of the scintillation light.

(Fourth Embodiment)

The fourth embodiment of the present invention will be described with reference to FIG. 7. It is however to be noted that the distribution-measuring apparatus according to this embodiment has numerous features common with the distribution-measuring apparatus according to the first embodiment of the present invention and, accordingly, in the following description, features and/or components similar to those of the distribution-measuring apparatus according to the first embodiment are not described to avoid repetition thereof and, instead, only differences from that according to the first embodiment will be described. Specifically, in the distribution-measuring apparatus according to the fourth embodiment, an optical filter is disposed in front of the image analyzer, while other features and/or components thereof are substantially identical with those in the distribution-measuring apparatus according to the first embodiment.

Figure 7:
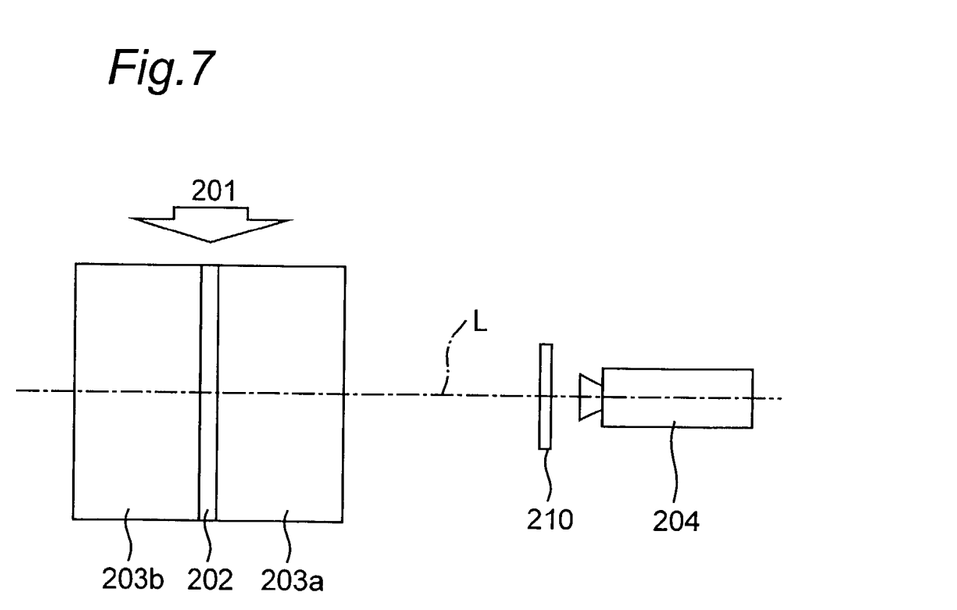
FIG. 7 is a side view of a distribution-measuring apparatus according to a fourth preferred embodiment of the present invention.

The optical filter referred to above and identified by 210 in FIG. 7 is of a kind effective to disturb passage therethrough of light of a wavelength longer and shorter than the emitted light wavelength of the plastic scintillator 202, that is, effective to allow passage therethrough of only light of the emitted light wavelength from the plastic scintillator 202. Specifically, in the absorption dose distribution measuring apparatus as shown in FIG. 7, radiation 201 such as X-rays or particle beams such as electron beams is projected onto the phantom constructed of the plate-type plastic scintillator 202, the transparent plastic block 203a and the plastic block 203b. A pattern of intensity distribution of light emitted from the plastic scintillator 202 is measured through the optical filter 210 by the image analyzer 204 such as, for example, a CCD camera.

The optical filter 210 is in the form of a bandpass filter operable to pass therethrough only light of the emitted light wavelength from the plastic scintillator 202. Accordingly, most of the Cerenkov light generated in the plastic scintillator 202 and the transparent plastic block 203a cannot pass through the optical filter 210. Because of this, light measured by the image analyzer 204 is mostly comprised of the scintillation light generated from the plastic scintillator 202. Accordingly, it is possible to reduce or eliminate the noise resulting from the Cerenkov light and, hence, to measure the absorbed dose accurately.

It is to be noted that the optical filter 210 that can be employed in the present invention may alternatively be a sharp cut filter operable to disturb passage therethrough of only light shorter than the emitted light wavelength of the plastic scintillator 202. Even in this case, effects generally similar to that afforded by the use of the bandpass filter can be obtained.

(Fifth Embodiment)

The fifth embodiment of the present invention will be described with reference to FIG. 8. It is however to be noted that the distribution-measuring apparatus according to this embodiment has numerous features common with the distribution-measuring apparatus according to the first embodiment of the present invention and, accordingly, in the following description, features and/or components similar to those of the distribution-measuring apparatus according to the first embodiment are not described to avoid repetition thereof and, instead, only differences from that according to the first embodiment will be described. Specifically, in the distribution-measuring apparatus according to the fifth embodiment, an optical filter made of a plastic material is interposed between the plastic scintillator 202 and the transparent plastic block 203a on one side adjacent the image analyzer 204, while other features and/or components thereof are substantially identical with those in the distribution-measuring apparatus according to the first embodiment.

Figure 8:
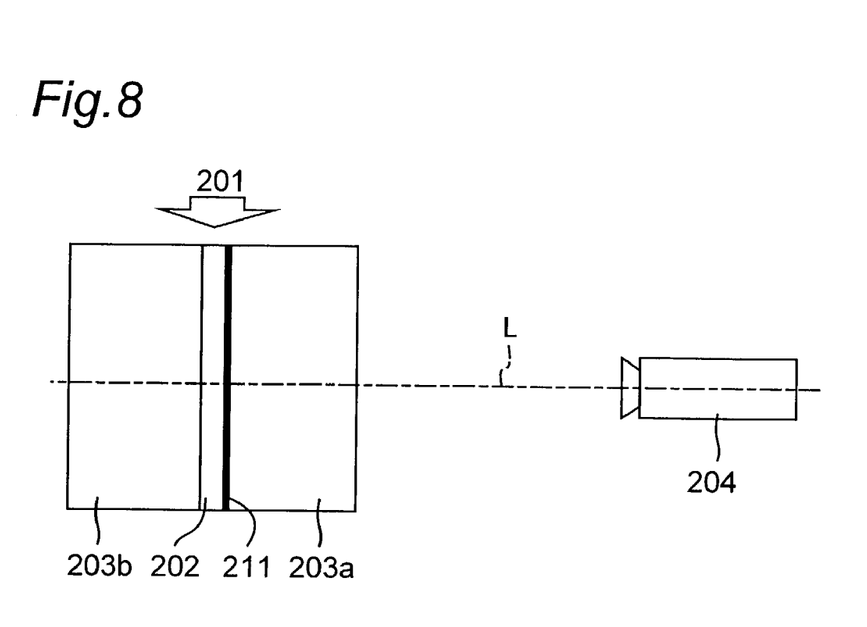
FIG. 8 is a side view of a distribution-measuring apparatus according to a fifth preferred embodiment of the present invention.

The optical filter referred to above and identified by 211 in FIG. 8 is of a kind effective to disturb passage therethrough of light of a wavelength longer and shorter than the emitted light wavelength of the plastic scintillator 202, that is, effective to allow passage therethrough of only light of the emitted light wavelength from the plastic scintillator 202. As shown in FIG. 8, in the distribution-measuring apparatus, radiation 201 such as X-rays or particle beams such as electron beams is projected onto the phantom constructed of the plate-type plastic scintillator 202, the transparent plastic block 203a and the plastic block 203b. A pattern of intensity distribution of light emitted from the plastic scintillator 202 is measured through the optical filter 211 by the image analyzer 204 such as, for example, a CCD camera. The optical filter 210 is in the form of a bandpass filter operable to pass therethrough only light of the emitted light wavelength from the plastic scintillator 202.

If the optical filter 211 were not employed, and when the Cerenkov light is generated from the transparent plastic block 203, there is the possibility that the plastic scintillator 202 may be excited by a short wavelength component of the Cerenkov light to emit light. Since the Cerenkov light has a light emitting characteristic quite different from the human body tissue, emission of the light from the scintillator as a result of excitation by the Cerenkov light will adversely affect measurement of the absorbed dose.

Accordingly, in order to prevent the plastic scintillator 202 from being excited by the Cerenkov light emitted from the transparent plastic block 203a, the optical filter 211 is interposed between the plastic scintillator 202 and the transparent plastic block 203a to thereby increase the accuracy of the absorption dose measurement. Material for the optical filter 211 must be compatible with the human body tissue since it is positioned at the site to be detected. Accordingly, the optical filter 211 should be made of a plastic material.

It is to be noted that the optical filter 210 that can be employed in the present invention may alternatively be a sharp cut filter operable to disturb passage therethrough of only light shorter than the emitted light wavelength of the plastic scintillator 202. Even in this case, effects generally similar to that afforded by the use of the bandpass filter can be obtained.

(Sixth Embodiment)

The sixth embodiment of the present invention will be described with reference to FIG. 9. It is however to be noted that the distribution-measuring apparatus according to this embodiment has numerous features common with the distribution-measuring apparatus according to the first embodiment of the present invention and, accordingly, in the following description, features and/or components similar to those of the distribution-measuring apparatus according to the first embodiment are not described to avoid repetition thereof and, instead, only differences from that according to the first embodiment will be described. Specifically, in the distribution measuring apparatus according to the sixth embodiment, the plastic block 203c positioned on one side of the plastic scintillator 202 remote from the image analyzer 204, or an interface portion of the plastic block 203c held in contact with the plastic scintillator 202 has a white color, while other features and/or components thereof are substantially identical with those in the distribution-measuring apparatus according to the first embodiment.

Figure 9:
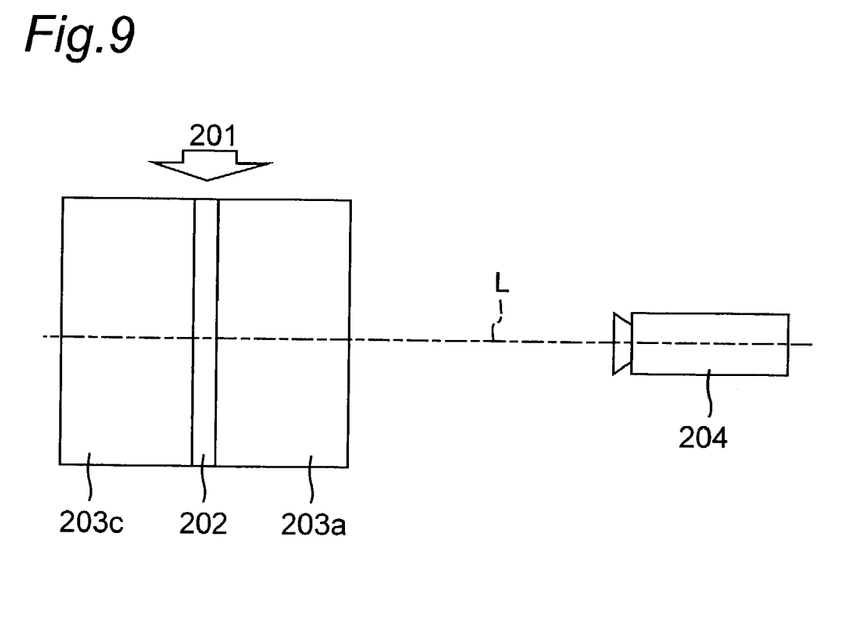
FIG. 9 is a side view of a distribution-measuring apparatus according to a sixth preferred embodiment of the present invention.

Referring particularly to FIG. 9, in the distribution-measuring apparatus shown therein, radiation 201 such as X-rays or particle beams such as electron beams is projected onto the phantom constructed of the plate-type plastic scintillator 202, the transparent plastic block (acrylic block) 203a positioned on one side of the plastic scintillator 202 adjacent the image analyzer 204, and the plastic block 203c positioned on the other side of the plastic scintillator 202 remote from the image analyzer 204 and having a white-colored interface portion held in contact with the plastic scintillator 202. A pattern of intensity distribution of light emitted from the plastic scintillator 202 is measured by the image analyzer 204 such as, for example, a CCD camera.

Since that interface portion of the plastic block 203c held in contact with the plastic scintillator 202 is white-colored, light emitted from the plastic scintillator 202 and traveling in a direction counter to the image analyzer 204 can be reflected so as to travel towards the image analyzer 204. Because of this, the efficiency of utilization of light can be increased, resulting in increase of the sensitivity.

(Seventh Embodiment)

The seventh embodiment of the present invention will be described with reference to FIG. 10. It is however to be noted that the distribution-measuring apparatus according to this embodiment has numerous features common with the distribution-measuring apparatus according to the first embodiment of the present invention and, accordingly, in the following description, features and/or components similar to those of the distribution-measuring apparatus according to the first embodiment are not described to avoid repetition thereof and, instead, only differences from that according to the first embodiment will be described. Specifically, in the distribution-measuring apparatus according to the seventh embodiment, the plastic block 203d positioned on one side of the plastic scintillator 202 remote from the image analyzer 204, or an interface portion of the plastic block 203d held in contact with the plastic scintillator 202 has a black color, while other features and/or components thereof are substantially identical with those in the distribution-measuring apparatus according to the first embodiment.

Figure 10:
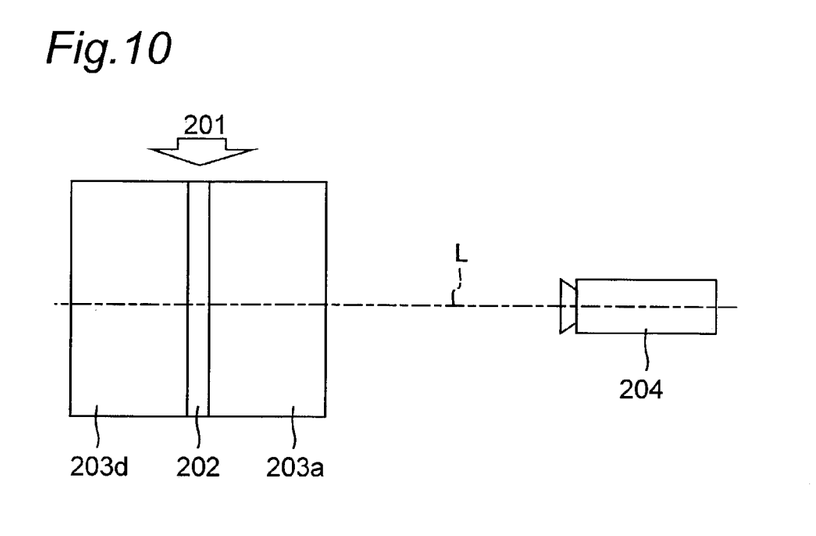
FIG. 10 is a side view of a distribution-measuring apparatus according to a seventh preferred embodiment of the present invention.

Referring particularly to FIG. 10, in the distribution-measuring apparatus shown therein, radiation 201 such as X-rays or particle beams such as electron beams is projected onto the phantom constructed of the plate-type plastic scintillator 202, the transparent plastic block (acrylic block) 203a positioned on one side of the plastic scintillator 202 adjacent the image analyzer 204, and the plastic block 203d positioned on the other side of the plastic scintillator 202 remote from the image analyzer 204 and having a block-colored interface portion held in contact with the plastic scintillator 202.

A pattern of intensity distribution of light emitted from the plastic scintillator 202 is measured by the image analyzer 204 such as, for example, a CCD camera.

Since that interface portion of the plastic block 203d held in contact with the plastic scintillator 202 is black-colored, irregular internal reflection of light within the plastic block 203d can be minimized or virtually eliminated. As a result thereof, the spatial resolving power can be increased, allowing a highly accurate absorption dose distribution measurement to be achieved.

(Eighth Embodiment)

The eighth embodiment of the present invention will be described with reference to FIG. 11. It is however to be noted that the distribution-measuring apparatus according to this embodiment has numerous features common with the distribution-measuring apparatus according to the first embodiment of the present invention and, accordingly, in the following description, features and/or components similar to those of the distribution measuring apparatus according to the first embodiment are not described to avoid repetition thereof and, instead, only differences from that according to the first embodiment will be described. Specifically, in the distribution-measuring apparatus according to the eighth embodiment, the plastic scintillator 202e or the plastic block 203e positioned on one side of the plastic scintillator 202e adjacent the image analyzer 204 has its peripheral side surface applied with a black-colored coating, while other features and/or components thereof are substantially identical with those in the distribution-measuring apparatus according to the first embodiment.

Figure 11:
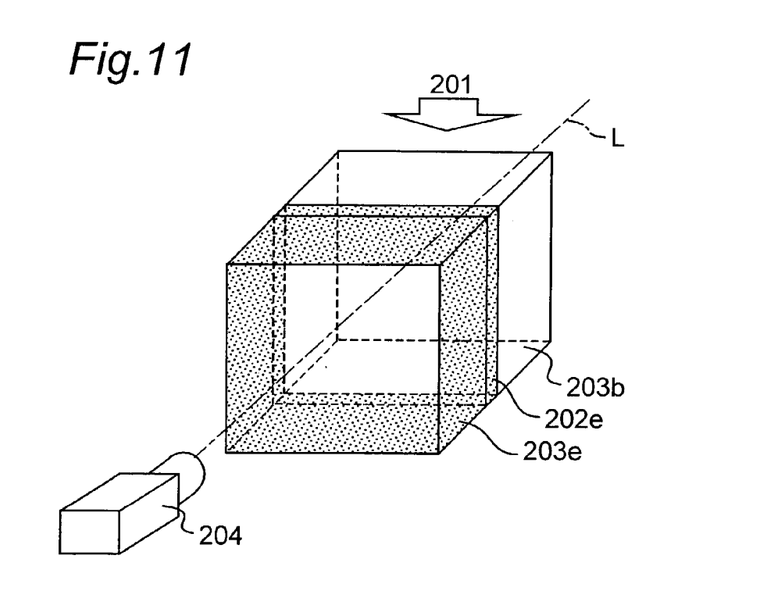
FIG. 11 is a side view of a distribution-measuring apparatus according to an eighth preferred embodiment of the present invention.

Referring particularly to FIG. 11, in the distribution-measuring apparatus shown therein, radiation 201 such as X-rays or particle beams such as electron beams is projected onto the phantom constructed of the plate-type plastic scintillator 202e, the transparent plastic block 203e and the plastic block 203b. A pattern of intensity distribution of light emitted from the plastic scintillator 202e is measured by the image analyzer 204 such as, for example, a CCD camera.

However, since the peripheral side surface of the plastic scintillator 202e is applied with the black-colored coating, it is possible to prevent light emitted within the plastic scintillator 202e from being reflected inside the scintillator 202e and subsequently entering the image analyzer 204. Accordingly, it is possible to reduce noise light resulting from reflection, to thereby allow a highly accurate absorption dose distribution measurement. If the peripheral side surface of the transparent plastic block 203e is applied with a black-colored coating in a manner similar to that of the plastic scintillator 202e, it is similarly possible to prevent light reflected inside the transparent plastic block (acrylic block) 203e from entering the image analyzer 204, to thereby allow a highly accurate absorption dose distribution measurement.

(Ninth Embodiment)

The ninth embodiment of the present invention will be described with reference to FIG. 12. It is however to be noted that the distribution-measuring apparatus according to this embodiment has numerous features common with the distribution measuring apparatus according to the first embodiment of the present invention and, accordingly, in the following description, features and/or components similar to those of the distribution-measuring apparatus according to the first embodiment are not described to avoid repetition thereof and, instead, only differences from that according to the first embodiment will be described. Specifically, in the distribution-measuring apparatus according to the ninth embodiment, the path of travel of light emitted by the plastic scintillator 202 is so bent as to allow it to be deflected at right angles towards the image analyzer 204, while other features and/or components thereof are substantially identical with those in the distribution-measuring apparatus according to the first embodiment.

Figure 12:
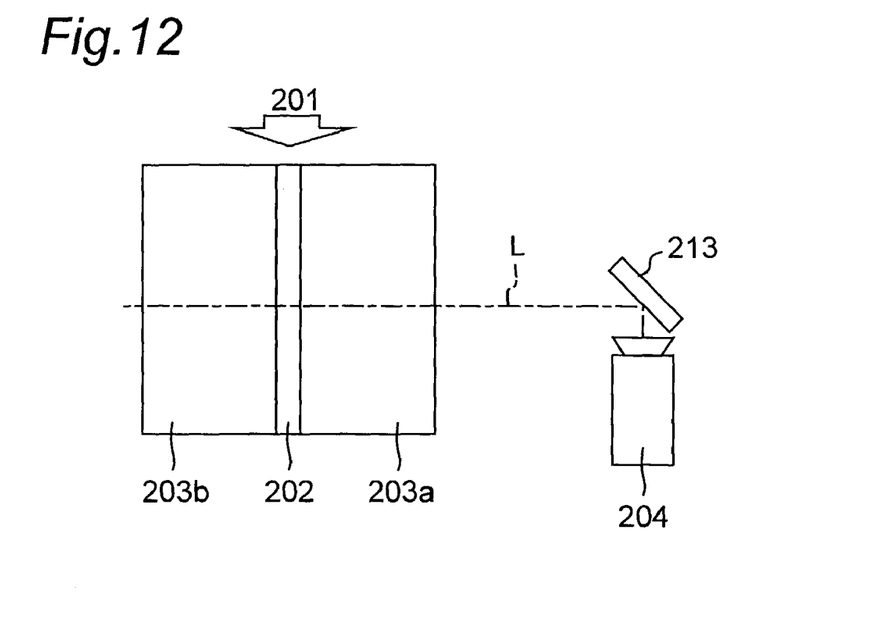
FIG. 12 is a side view of a distribution-measuring apparatus according to a ninth preferred embodiment of the present invention.

Referring to FIG. 12, in the distribution-measuring apparatus shown therein, radiation 201 such as X-rays or particle beams such as electron beams is projected onto the phantom constructed of the plate-type plastic scintillator 202, the transparent plastic block 203a and the plastic block 203b. A pattern of intensity distribution of light emitted from the plastic scintillator 202 is measured by the image analyzer 204 such as, for example, a CCD camera.

As shown in FIG. 12, the path of travel of light L extending from the phantom to the image analyzer 204 is bent 90° by a deflecting mirror 213 and, accordingly, the light L from the plastic scintillator 202 when impinging upon the deflecting mirror 213 is bent at right angles so as to be incident on the image analyzer 204. By properly arranging the phantom (constructed of the plastic scintillator 202 and the plastic blocks 203a and 203b) in the manner described above, the distribution-measuring apparatus as a whole can be assembled compact in size.

(Tenth Embodiment)

The tenth embodiment of the present invention will be described with reference to FIG. 13. It is however to be noted that the distribution-measuring apparatus according to this embodiment has numerous features common with the distribution-measuring apparatus according to the first embodiment of the present invention and, accordingly, in the following description, features and/or components similar to those of the distribution measuring apparatus according to the first embodiment are not described to avoid repetition thereof and, instead, only differences from that according to the first embodiment will be described. Specifically, in the distribution-measuring apparatus according to the tenth embodiment, the use is made of a linear drive device 214 for driving the phantom and the image analyzer 204 in a direction parallel to a direction across the thickness of the scintillator 202, while other features and/or components thereof are substantially identical with those in the distribution measuring apparatus according to the first embodiment.

Figure 13:
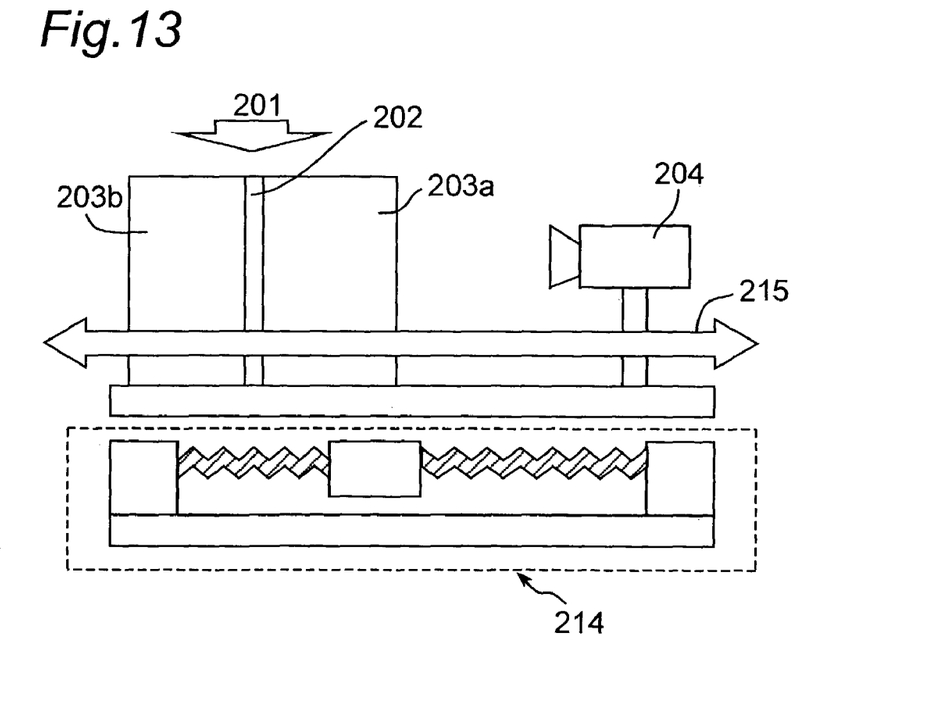
FIG. 13 is a side view of a distribution-measuring apparatus according to a tenth preferred embodiment of the present invention.

Referring particularly to FIG. 13, in the distribution-measuring apparatus shown therein, radiation 201 such as X-rays or particle beams such as electron beams is projected onto the phantom constructed of the plate-type plastic scintillator 202, the transparent plastic block 203a and the plastic block 203b. A pattern of intensity distribution of light emitted from the plastic scintillator 202 is measured by the image analyzer 204 such as, for example, a CCD camera.

The phantom and the image analyzer 204 are simultaneously driven by the linear drive device 214 in a direction shown by the arrow 215 and conforming to the direction across the thickness of the scintillator 202, that is, in a direction perpendicular to an end face (scintillator surface) of the scintillator 202, that is, in a direction shown by the arrow 215. While with the plate-type plastic scintillator 202 the pattern of distribution of the absorbed dose in the two dimensional plane can readily be measured, measurement of the absorbed dose distribution by driving the phantom and the image analyzer 204 linearly in the direction 215 makes it possible to measure the absorbed dose distribution in the three dimensional plane within a rectangular parallelepiped area encompassing the plastic scintillator 202.

It is to be noted that the length of time required to complete the three dimensional measurement can be reduced if measurement of the dose distribution in the two dimensional plane and the timing of drive of the phantom and the image analyzer 204 are properly controlled, for example, if the drive is chosen to be a continuous linear movement and the image measurement is performed by a motion picture taking.

Although the present invention has been described in connection with the preferred embodiments thereof with reference to the accompanying drawings, it is to be noted that various changes and modifications are apparent to those skilled in the art. Such changes and modifications are to be understood as included within the scope of the present invention as defined by the appended claims, unless they depart therefrom.

What is claimed is:

1. An apparatus for measuring absorption dose distribution, said apparatus comprising:
    a phantom including
        a plastic plate scintillator having surfaces and a thickness between the surfaces within a range from 0.15 to 1 mm, the thickness being determined by optical characteristics of the surfaces, limiting crosstalk in a direction perpendicular to thickness direction of the plastic plate scintillator to not more than 1 percent, and providing a spatial resolving power of 1 mm, and
        first and second plastic blocks positioned on opposite sides of said plastic plate scintillator in the direction of the thickness of said plastic plate scintillator, sandwiching said plastic plate scintillator, at least one of said first and second plastic blocks being transparent; and
    an image analyzer for measuring intensity distribution of light emitted from said plastic plate scintillator when said phantom is irradiated with radiation.

2. The apparatus according to claim 1, wherein the light emitted by said plastic plate scintillator is converted into an absolute value of an absorption dose rate.

3. The apparatus according to claim 1, wherein the surfaces of said plastic plate scintillator are polished to have optical characteristics of optical mirror surfaces.

4. The apparatus according to claim 1, wherein the light emitted by said plastic plate scintillator has a wavelength within the visible region of light, ranging from a green wavelength region to a red wavelength region.

5. The apparatus according to claim 1, further comprising a first optical filter disposed between said image analyzer and said phantom, said first optical filter disturbing passage of light having a wavelength shorter than the wavelength of the light emitted by said plastic plate scintillator.

6. The apparatus according to claim 5, further comprising a second optical filter disposed between said image analyzer and said phantom, said second optical filter disturbing passage of light having a wavelength longer than the wavelength of the light emitted by said plastic plate scintillator.

7. The apparatus according to claim 1, further comprising a plastic optical filter, wherein the one of said first and second plastic blocks that is positioned on a first side of said plastic plate scintillator and adjacent said image analyzer is transparent, and said optical filter is disposed between said transparent block and said image analyzer and disturbs passage of light having a wavelength shorter than the wavelength of the light emitted by said plastic plate scintillator.

8. The apparatus according to claim 7, further comprising an optical filter disposed between said image analyzer and said phantom, said optical filter disturbing passage of light having a wavelength shorter than the wavelength of the light emitted by said plastic plate scintillator.

9. The apparatus according to claim 1, wherein the one of said first and second plastic blocks that is positioned on the side of said plastic scintillator remote from said image analyzer is white in color.

10. The apparatus according to claim 1, wherein the one of said first and second plastic blocks that is positioned on the side of said plastic scintillator remote from said image analyzer is black in color.

11. The apparatus according to claim 1, wherein said plastic plate scintillator has a side surface with a black coating.

12. The apparatus according to claim 1, wherein the one of said first and second plastic blocks that is positioned on the side of said plastic scintillator adjacent said image analyzer is transparent and has a side surface with a black coating.

13. The apparatus according to claim 1, further comprising a linear drive mechanism for linearly driving said phantom and said image analyzer in the direction of the thickness of said plastic plate scintillator.

14. The apparatus according to claim 1, wherein the surfaces of said plastic plate scintillator have optical characteristics of light scattering surfaces.

* * * * *